US006972419B2

(12) United States Patent
Tejnil

(10) Patent No.: US 6,972,419 B2
(45) Date of Patent: Dec. 6, 2005

(54) EXTREME ULTRAVIOLET RADIATION IMAGING

(75) Inventor: Edita Tejnil, San Carlos, CA (US)

(73) Assignee: Intel Corporation, Santa Clara, CA (US)

( * ) Notice: Subject to any disclaimer, the term of this patent is extended or adjusted under 35 U.S.C. 154(b) by 333 days.

(21) Appl. No.: 10/373,415

(22) Filed: Feb. 24, 2003

(65) Prior Publication Data
US 2005/0243390 A1 Nov. 3, 2005

(51) Int. Cl.[7] ............................................. G01N 21/88
(52) U.S. Cl. .................. 250/492.2; 359/361; 359/350; 356/237.2
(58) Field of Search ................ 250/492.2; 359/361, 359/350; 356/237.2

(56) References Cited

U.S. PATENT DOCUMENTS

2003/0043370 A1 * 3/2003 Goldberg .................. 356/237.5
2003/0058529 A1 * 3/2003 Goldstein .................... 359/361
2003/0067598 A1 * 4/2003 Tomie ...................... 356/237.2

OTHER PUBLICATIONS

Yulin et al., "Spectral reflectance tuning of EUV mirrors for metrology applications," Proc. of SPIE, vol. 5037, 2003, pp. 286-293.

* cited by examiner

Primary Examiner—Nikita Wells
Assistant Examiner—Zia R. Hashmi
(74) Attorney, Agent, or Firm—Fish & Richardson P.C.

(57) ABSTRACT

An extreme (EUV) lithography system includes optical elements which vary the wavelengths of radiation as a function of the angle of incidence on a mask to maximize the reflected radiation intensity.

31 Claims, 5 Drawing Sheets

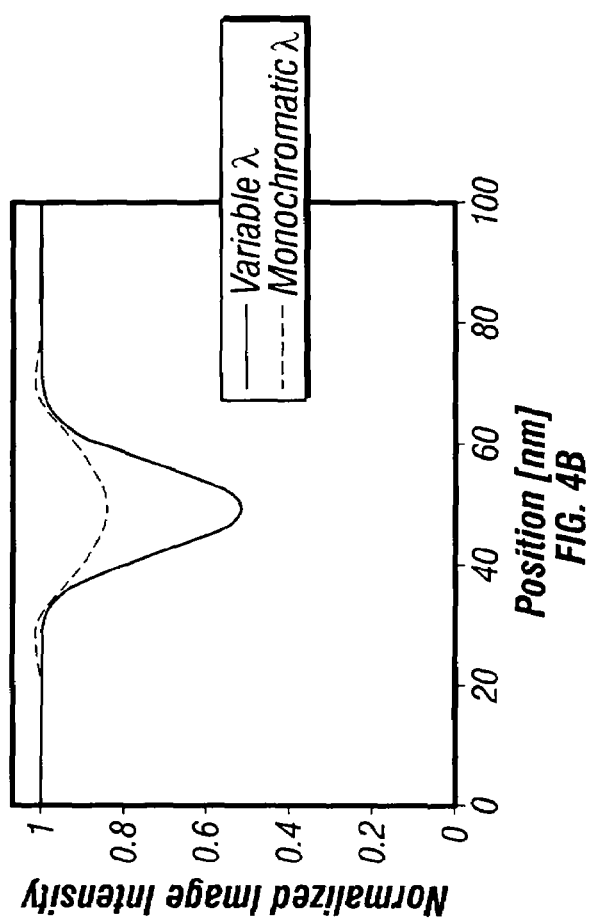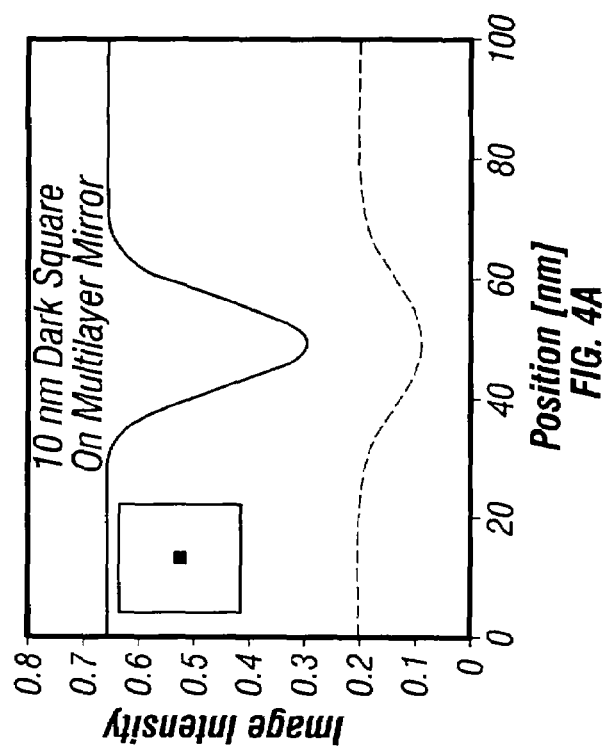

EXTREME ULTRAVIOLET RADIATION IMAGING

BACKGROUND

Photolithography uses an imaging system that directs radiation onto a patterned mask to form an image that is projected onto a semiconductor wafer covered with a light-sensitive photoresist. Photolithography production and inspection systems require increased optical resolving power to transfer increasingly smaller patterns and to identify increasingly smaller defects. Because optical resolving power is proportional to the wavelength of light, a light source with a shorter wavelength provides better optical resolution capability. Extreme ultraviolet lithography (EUVL) is a process that uses extreme ultraviolet (EUV) radiation which may be used in the manufacture and inspection of microelectronic semiconductor devices with feature sizes less than 100 nm.

BRIEF DESCRIPTION OF THE DRAWINGS

FIG. 4A illustrates image intensity as a function of the position of an image of a 10 nm square formed on a multi-layer reflective mask.

FIG. 4B illustrates the image intensity of FIG. 4A when the background intensity is normalized.

Like reference symbols in the various drawings indicate like elements.

DETAILED DESCRIPTION

EUV radiation is strongly absorbed by materials and gases. Imaging systems that utilize EUV radiation generally include multiple all-reflective optics to successively transmit beams of radiation to form an image of an object. Reflective elements in such systems may be coated with multi-layer thin films.

The reflective elements may include mirrors and reflective masks, or reticles, suitable for use with EUV radiation. Multi-layer coated EUV masks may be reflective for a limited range of wavelengths and incidence angles. In mask metrology systems, the narrow reflection passband may limit the effective numerical aperture of an optical system used to image features on the mask when nearly monochromatic radiation is used. This limitation affects the resolution of actinic metrology systems used to inspect EUVL reflective masks for defects subsequent to multi-layer deposition. In EUV optical systems the limited reflection passband of the reflective mask, and other reflective elements such as mirrors, effectively reduces the overall spectral passband of the system. This reduction affects the amount of useful EUV radiation that can be transferred from the radiation source to an imaging target, such as a wafer or a detector.

In an embodiment, these issues are addressed by modulating radiation wavelength and the incident angle of the radiation on a reflective mask in EUVL metrology, inspection or lithography systems. The transmission of discreet wavelengths, each corresponding to a particular incident angle, may increase the maximum useable numerical aperture, and hence the maximum resolution, of an EUV optical system.

Figure 1A:
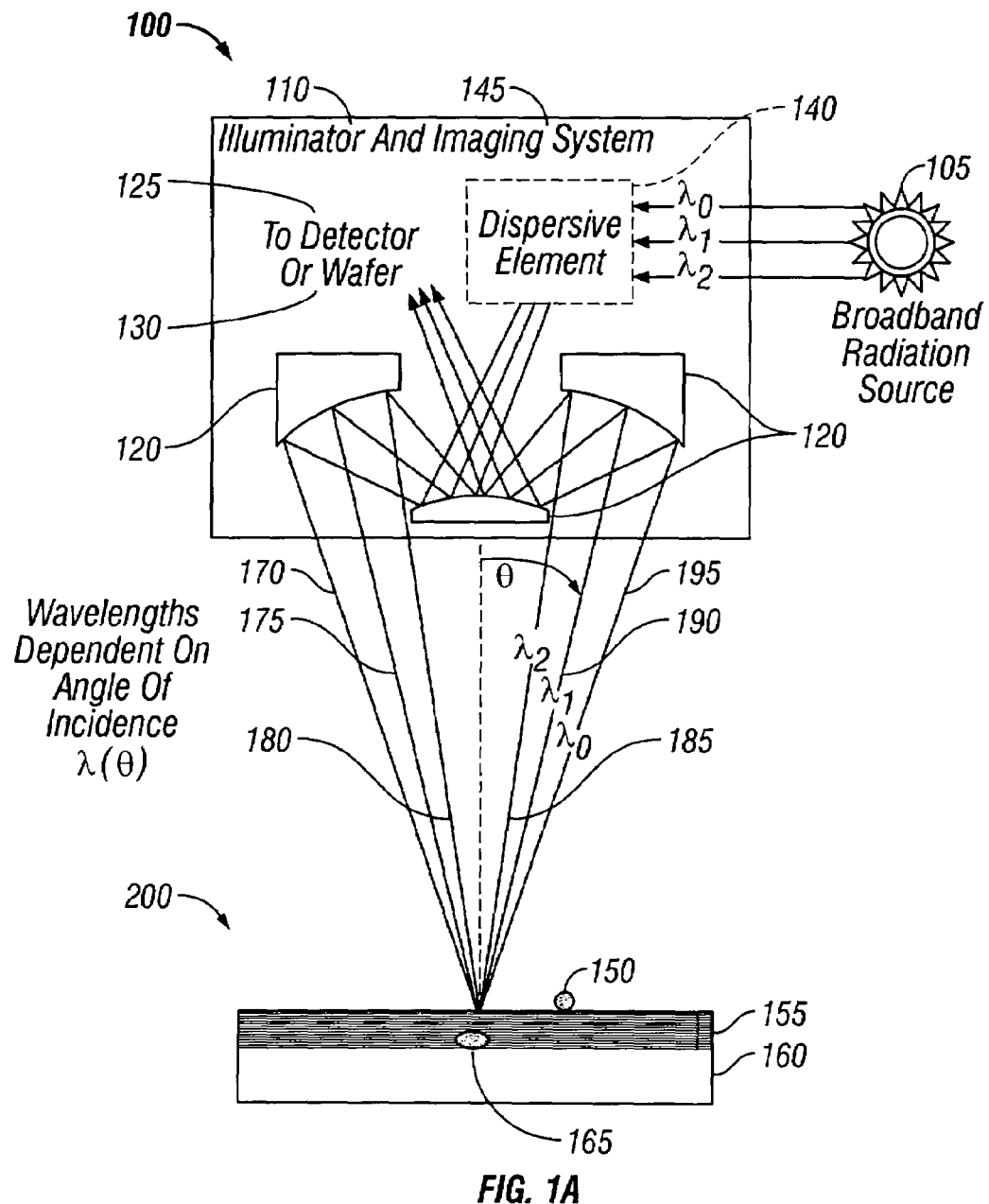
FIG. 1A is a diagram of an optical imaging system.
Figure 1B:
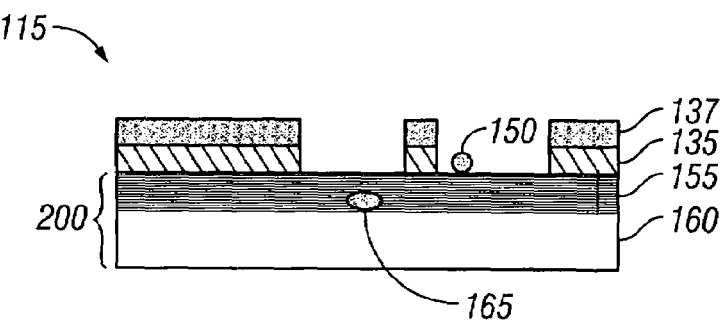
FIG. 1B is a diagram of a patterned reflective mask.

Referring generally to FIG. 1A and FIG. 1B, an EUV optical system 100 includes a radiation source 105, an illuminator 110, an imaging system 145, a reflective patterned mask 115 or reflective mask blank 200 positioned intermediate to the illuminator and imaging system, a plurality of reflective mirrors 120, a detector 125 for detecting an image or a wafer 130 for patterning, and an optional spectrally dispersive optical element 140 positioned intermediate to the radiation source 105 and the patterned mask 115 or mask blank 200. As used herein, the term "mask" encompasses reflective patterned masks 115 and reflective mask blanks 200.

The radiation source 105 may be any source able to produce radiation in the extreme ultraviolet (EUV) wavelength range. Generally, EUV radiation has a wavelength (λ) between approximately 4 to 30 nm and may be produced by any suitable means including laser produced plasma, synchrotron radiation, electric discharge sources, high-harmonic generation with femto-second laser pulses, discharge-pumped x-ray lasers, and electron-beam driven radiation devices. Laser-produced plasma sources focus an intense pulsed laser beam onto a target to produce radiation with a broad emission spectrum. Suitable targets are noble gases and metals, such as gold, tantalum, tungsten, and copper.

The radiation source 105 provides broad bandwidth EUV radiation. In one implementation, the radiation source 105 further provides an angular emission spectrum that varies with the emission wavelength. In another implementation, a spectrally dispersive optical element 140 is positioned subsequent to the radiation source 105. One example of a suitable radiation source 105 is a plasma created when a laser, such as a 1700 Watt (W) pulsed ytterbium-aluminum-garnet (YAG) solid-state laser, illuminates a gas, such as a supersonic jet of xenon gas. As another example, a suitable radiation source 105 can be formed using bending magnets and undulators associated with synchrotrons. As a further example, a suitable radiation source 105 may be formed or developed from discharge sources, which have the potential to provide adequate power in the desired wavelength range. EUV radiation is strongly absorbed in virtually all materials transmissive to visible light, including gases and glass. For this reason, EUV imaging may be carried out in a near vacuum.

A spectrally dispersive optical element 140 may be a device that collects a spectral band of radiation from source 105 and transmits or reflects radiation comprising a plurality of wavelengths to different directions. Such devices include diffraction gratings. A grating may be composed of a set of parallel lines, e.g., ridges, grooves, or other structures with a two-dimensional cross section. This linear diffraction grating generates diffraction or scattering that is perpendicular to the lines. In the event the lines are all identical and equally spaced, the radiation will be diffracted only in a few discrete angles. In general, a grating can be reflective and used at grazing incidence. The surface of such a grating can be patterned lithographically.

Diffraction gratings may be superimposed with a precise pattern of microscopic periodic structures. These may be in a pattern of corrugated surface grooves (a surface-relief grating), though some gratings are formed by the periodic variation of the refractive index inside the grating itself (i.e., a volume grating). Gratings used to disperse ultraviolet (UV) and visible light may contain about 10 to 50,000 grooves per millimeter, about 20 to 10,000 grooves per millimeter or about 30 to 3000 grooves per millimeter. Generally, the distance between adjacent grooves may be on the order of one micron. Diffraction gratings may be either ruled or holographic, although there is a wider range of groupings within each style.

Ruled diffraction gratings may be produced by physically forming grooves into a reflective surface with a diamond mounted on a ruling engine. The distance between adjacent grooves and the angle the grooves form with respect to the substrate influence both the dispersion and efficiency of a grating. Diffraction gratings can be ruled on a variety of substrates, for example, glass, metal and ceramic.

Holographic diffraction gratings are formed when a series of interference fringes, corresponding to the grooves of the desired grating, are recorded on a photosensitive layer, and the subsequent chemical treatment forms a modulated profile on the surface of the blank by selective dissolution. The pattern may subsequently be transferred into the grating surface by an etch. This particular type of diffraction grating includes many configurations, such as planar, curved (e.g., concave and toroidal), or aberration-corrected, with uniform and non-uniform groove spacing. Non-uniform spacing can provide superior focusing characteristics. Holographic gratings may be useful for visible and UV radiation and generally exhibit less stray light and "ghost" spectra than do classically ruled gratings, because they have fewer random and systematic imperfections.

The mask 115, 200 may be planar, concave, convex, or any suitable shape to permit inspection or patterning. In general, an EUVL mask is planar.

The illuminator section 110 transmits the radiation from the source 105 to the mask 115, 200. The illuminator 110 may include condenser mirrors which collect and focus the radiation from the source 105 onto the mask 115, 200.

The imaging system 145 may transfer the image from the mask 115, 200 and form the image onto an imaging target such as a detector 125 or a wafer 130. For example, when the mask is a mask blank 200, the image may be formed on a detector 125 such that any imperfections in the mask blank 200 can be detected. When the mask is a patterned mask 115, the image may be formed on a detector such that any imperfections in the pattern, any defects on the surface, or any defects in the blank not covered by the pattern can be detected. The imaging system optics may include mirrors 120 that project radiation from the mask 115, 200 onto an imaging target. The reflectance spectrum of the mask 115, 200 may be matched to that of the reflective mirrors 120 in the imaging system 145.

The present system utilizes graded multi-layer coated reflective optics as opposed to uniform thickness multi-layer coated optics. Uniform thickness multi-layer coatings are generally not suitable for a wide range of incidence angles. A graded reflective coating can be applied to an optical mirror so that the reflectivity at a given incidence point of a radiation beam is modified. The modification provides a reflected beam having an intensity equal to that of other reflected beams.

Referring generally to FIG. 1A, during fabrication of the mask blank 200, defects 150, 165 can be formed in the multi-layer reflector 155. The multi-layer reflector 155 may be deposited on substrate 160 to form mask blank 200. Defect 165 may have been introduced into the mask blank 200 by a surface blemish on the substrate 160 and defect 150 may have been introduced into the mask blank 200 during deposition of the multi-layer reflector 155 or from surface contamination of the mask blank 200.

The mask blank 200 may be inspected for defects formed in the multi-layer reflector 155 by actinic inspection using wavelengths consistent with wavelengths used by a photolithography system that may accommodate a reflective mask. As discussed below, the wavelengths incident on the mask blank 200 can correspond to specific angles of incidence on the mask blank.

If the mask blank defects are unacceptable, then the mask blank 200 is rejected. If the mask blank is acceptable, then a pattern is replicated into an absorber layer 137 and a buffer layer 135 deposited on the mask blank. As shown in FIG. 1B, the invention encompasses detecting imperfections in a patterned mask 115 in addition to a mask blank 200. Regarding FIG. 1B, the buffer layer 135 is etched in locations not covered by the etched absorber pattern to produce the patterned mask 115. The fabricated patterned mask 115 can be inspected by a suitable inspection technique, such as actinic inspection using wavelengths consistent with wavelengths used by a photolithography system that can accommodate a reflective mask. As discussed below, the wavelengths incident on the patterned mask 115 can correspond to specific angles of incidence on the mask.

The substrate 160 may be any substrate that can endure subsequent fabrication processes and is typically made of a material having a low thermal expansion, such as, for example, ULE™, an ultralow expansion titanium silicate glass made by Corning Corporation of New York. Referring generally to FIG. 1A and FIG. 1B, any radiation incident on the mask 115, 200 (represented by rays 170, 175 and 180 in FIG. 1A) will be reflected or partially reflected (represented by lines 195, 190 and 185 in FIG. 1A) by the multi-layer reflector 155 in a non-patterned region of a patterned mask 115 (FIG. 1B) or by the multi-layer reflector 155 in a mask blank 200.

The reflectance spectrum of the mask 115, 200 may be matched to that of the multi-layer coated mirrors in the imaging system. The multi-layer coatings consist of alternating layers of materials having dissimilar EUV optical constants, and they provide a resonant reflectivity when the period of the layers is approximately $\lambda/2$.

A number of different combinations of reflective and transmissive materials may be used. In one implementation, for systems operating at-wavelengths of about 13 nm, the materials are molybdenum (Mo) and silicon (Si). In another implementation, multiple layers of Mo and beryllium (Be) are used as multi-layer coating systems for systems operating at about 11 nm. In general, reflective optics in EUVL systems have about 40 alternating layer pairs of reflective and transmissive materials, such as Mo:Si or Mo:Be. In other implementations, more than two materials may be used to form each period of the multi-layer stack, such as a thin layer of $B_4C$ between Mo and Si to stabilize the Mo:Si interface.

The angle of incidence $\theta$ of off-axis radiation is determined from normal to the mirror surface. Each off-axis radiation wavelength $\lambda_0$ 170, $\lambda_1$ 175, and $\lambda_2$ 180 corresponds to a particular angle of incidence on a multi-layer reflective surface, such as those associated with a mask 115, 200 or a mirror 120. Reflected radiation $\lambda_0$ 195, $\lambda_1$ 190, and $\lambda_2$ 185 is transmitted to imaging system 145 and ultimately to an imaging target such as a detector 125 or a wafer 130.

Figure 2A:
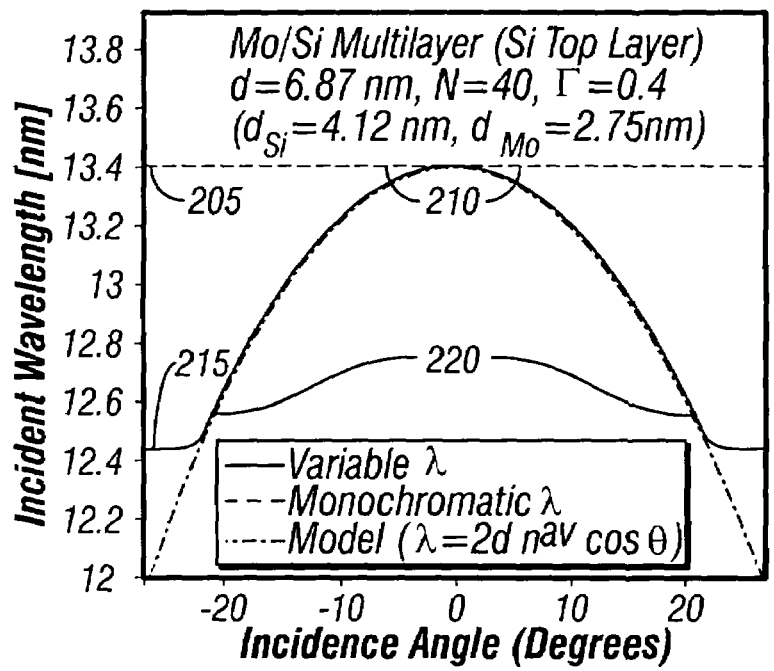
FIG. 2A illustrates radiation wavelength as a function of the angle of incidence at a multi-layer reflective element.

Referring to FIG. 2A, the desired wavelength can be determined as a function of the incidence angle by the formula $\lambda = 2d\, n_{avg} \cos \theta$, where $n_{avg}$ is the real part of the average index of refraction at the wavelength $\lambda$ of the materials that make up the multi-layer, d is the period of the reflective coating, and $\theta$ is the incident angle of wavelength $\lambda$. Using monochromatic radiation at a wavelength of approximately 13.4 nm 205, the calculated optimal reflectivity of an exemplary reflective element comprised of Mo/Si multi-layer with d=6.87 nm, N (number of layers) =40, and $\Gamma$=0.4 (where $\Gamma$ is the ratio of the thickness of the Mo and Si layers in the multi-layer period d) is only obtainable if the incident angle of the radiation is no more than about 5° off-axis 210. In contrast, when the wavelength is controlled for all angles of incidence 215, maximum resolution is attainable at angles of incidence exceeding about 20° using a wavelength of about 12.6 nm 220.

Figure 2B:
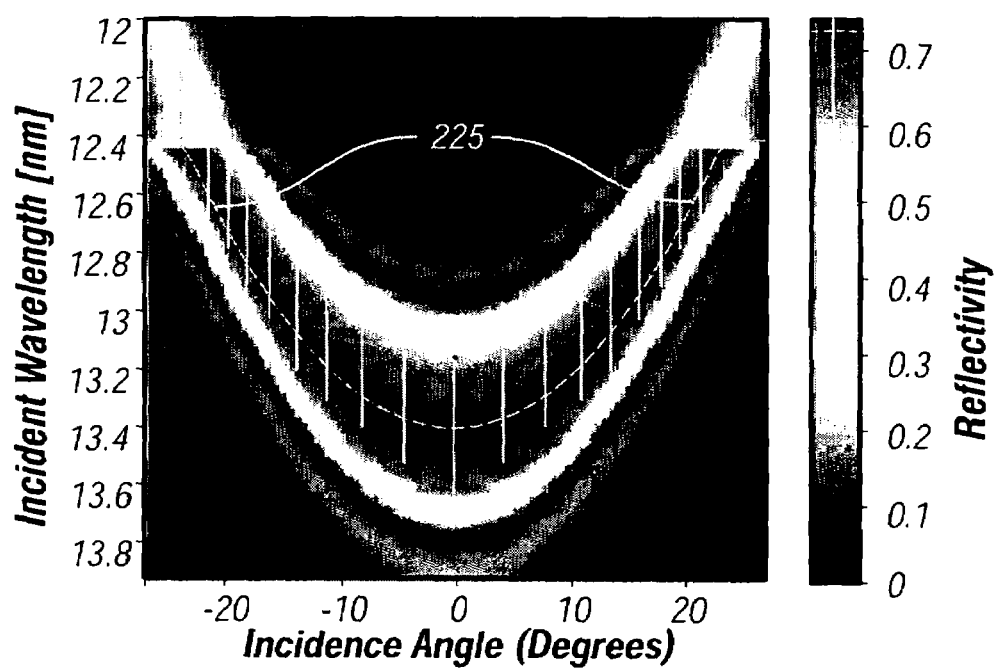
FIG. 2B illustrates the effect of radiation wavelength and angle of incidence on reflectivity of an exemplary multi-layer reflective element.

Referring to FIG. 2B, the desired angle dependent wavelength can also be determined from the empirically-determined reflectivity of a multi-layer coated reflective element. In FIG. 2B, the region of maximum reflectance (indicated by the horizontal and vertical white lines in FIG. 2B) extends from a wavelength of about 13.6 nm to 12.4 nm, as determined from the exemplary Mo/Si multi-layer coated reflective element having the characteristics presented FIG. 2A. At an incident angle between 10° and 20° off-axis, wavelength from about 13.2 to 12.4 nm provide reflectivity of between about 60 to 70% 225. Since the maximum theoretical reflectivity of a multi-layer mirror made of Mo/Si is approximately 72%, the present system of varying wavelength with incident angle provides an overall reflection passband that is larger than conventional systems utilizing monochromatic radiation. It is understood that additional wavelengths corresponding to particular incident angles can be determined for alternative multi-layer coatings, such as Mo/Be.

Figure 3A:
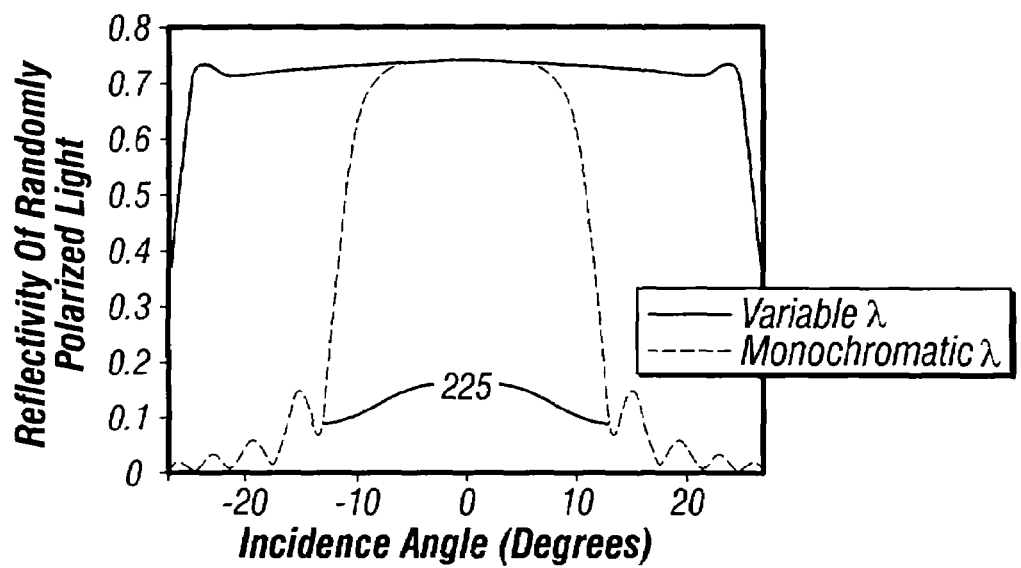
FIG. 3A illustrates reflectivity as a function of the angle of incidence of monochromatic or variable wavelength radiation at an exemplary multi-layer reflective element.
Figure 3B:
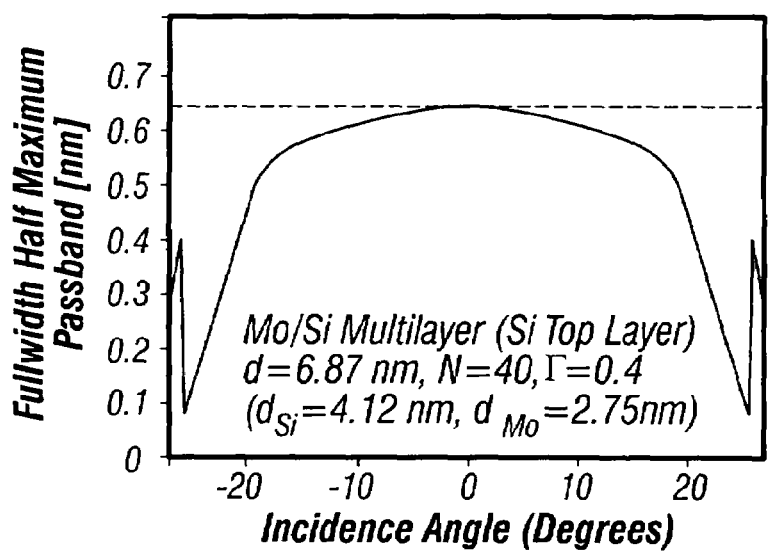
FIG. 3B illustrates the spectral bandwidth control for FIG. 3A.

Referring to FIGS. 3A and 3B, the reflectivity of a Mo/Si multi-layer coated sample as a function of incidence angle is provided. Modifying radiation wavelength in relation to incident radiation angle on a reflective surface provides an overall reflection passband that is increased in comparison to conventional monochromatic approach or other approaches that sacrifice bandwidth for multi-layer and optical system simplicity. A system that implements a method of varying wavelength with incident angle will increase the reflectivity of off-axis radiation and thereby improve maximum resolution and power efficiency of the system. For example, since monochromatic radiation at an angle >12° from normal axis is not reflected 225 (FIG. 3A), an optical device, such as microscope, utilizing such radiation will have a calculated maximum effective numerical aperture of about 0.21. In contrast, an optical device with specially designed angle and wavelength spectra that can vary wavelength with incident angle will have a calculated maximum effective numerical aperture of about 0.42. For Mo/Si multi-layers, the maximum numerical aperture can be even larger if the nominal operating wavelength is larger than 13.4 nm, in order to avoid wavelengths shorter than the silicon absorption edge around 12.4 nm.

Figure 4D:
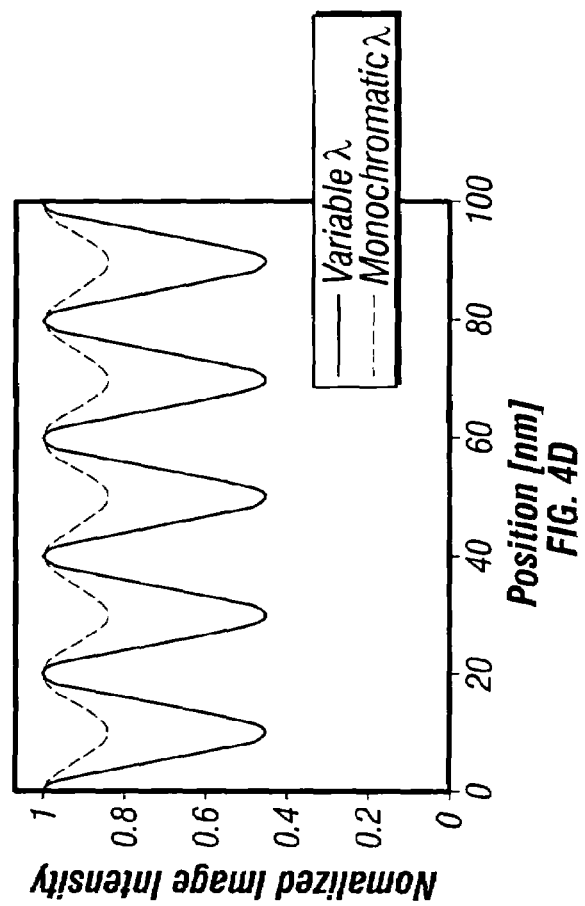
FIG. 4D illustrates the image intensity of FIG. 4C when the background intensity is normalized.

Referring to FIGS. 4A–4D, mask images formed by an EUV microscope using monochromatic radiation and an EUV microscope with specific wavelength and angle spectra are provided. The masks are illuminated with an objective having a numerical aperture of 0.45 with a partial coherence factor $\sigma$ of 1. FIG. 4A compares the image intensity of a 10 nm dark square when illuminated with monochromatic radiation or radiation with specific wavelength and angle spectra. In FIG. 4B, images generated with monochromatic radiation or radiation with specific wavelength and angle spectra are normalized to the same background intensity.

Figure 4C:
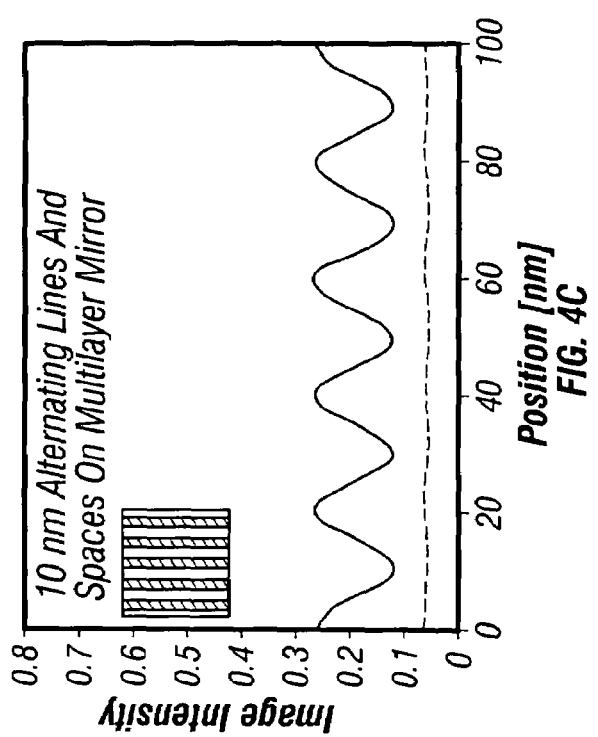
FIG. 4C illustrates the image intensity as a function of the position of an image of 10 nm equal lines and spaces on a multi-layer reflective mask.

FIG. 4C compares the image intensity of 10 nm alternating lines and spaces when illuminated with monochromatic radiation or radiation with specific wavelength and angle spectra. In FIG. 4D, images generated with monochromatic radiation or radiation with specific wavelength and angle spectra are normalized to the same background intensity.

The relative difference in power efficiency when modulating radiation wavelength and angle spectra or using monochromatic radiation is apparent in FIGS. 4A and 4C. The image intensity is increased for both the square image and alternating lines image when wavelength is modified according to incident angle. Thus, modulating radiation wavelength and angle spectra provides increased radiation throughput (i.e., increased power efficiency) over the use of monochromatic radiation. Similarly, differences in resolution are evident from the data provided in FIGS. 4B and 4D when the images are normalized to the same background intensity. The increased efficiency of such a system provides a mechanism for transferring an image of a patterned mask to a wafer using less power. Alternatively, increased efficiency provides a mechanism for decreasing the time required for transferring an image from a patterned mask to a wafer during the photolithography process.

Referring generally to FIG. 1A and FIG. 1B, EUVL mask fabrication requires that the mask blank 200 or patterned mask 115 be essentially defect free. Generally, the mask may include less than 0.003 defects per square centimeter (cm) at a defect size greater than 30 nm. The narrow passband of a multi-layer coating effectively limits the maximum numerical aperture and resolution of an optical system that utilizes nearly monochromatic illumination. Therefore, high-resolution at-wavelength inspection systems are preferred.

The mask blank 200 or patterned mask 115 may be inspected using any suitable inspection technique such as, for example, optical inspection using reflected light or actinic inspection, which uses radiation at a wavelength used by the photolithography imaging system to image the patterned mask on the semiconductor wafer. For example, if the mask 115, 200 were to be used in the photolithography imaging system 100 (FIG. 1A), the actinic wavelength would be the wavelength output from the radiation source 105. In general, the inspection technique may be any technique that searches the mask for imperfections or either directly or indirectly emulates the photolithography imaging system used to image the patterned mask on the semiconductor wafer. Such systems can include scanning systems such as microscopes and interferometers that can detect imperfections in a reflective mask.

In one implementation, an at-wavelength EUVL optical system may be provided for EUVL mask inspection. The optical system may modulate radiation wavelength as a function of the angle of incidence on the reflective elements in the system, such as a mirror or reflective mask, to maximize the reflected radiation intensity and increase image resolution.

Referring generally to FIG. 1A and FIG. 1B, off-axis radiation having specific incident angles on reflective elements in the optical system, including the mask blank 200 or reflective mask 115, have wavelengths of $\lambda_0$ 170, $\lambda_1$ 175, and $\lambda_2$ 180. The wavelengths of $\lambda_0$, $\lambda_1$, and $\lambda_2$ are determined by their individual incident angles and the properties of the reflective multi-layers forming the reflective elements in the system, such as mirrors or a reflective mask 115, 200. For example, a mask blank 200 comprised of alternating layers of Mo/Si or Mo and Be, or Mo, $B_4C$ and Si, with characteristics similar to those provided in FIG. 2, can be positioned in a system shown in FIG. 1A. The off-axis wavelength at position $\lambda_0$ 170 can have an incident angle of 20°. Accordingly, the wavelength of $\lambda_0$ can be calculated by the formula $\lambda = 2d\ n_{avg} \cos \theta$.

Alternatively, the wavelength of $\lambda_0$ can be determined empirically. As exemplified in FIG. 2B, at an incident angle of about 20°, 60–70% reflectivity is obtained 225 when a wavelength of about 12.8 nm to 12.4 nm is used to illuminate the mask.

Referring to FIG. 1A, the reflected radiation 185, 190, 195 comprising an image of the defect associated with the mask is transmitted to an imaging system 145 and subsequently to an imaging target, such as a detector 125. The detector is an optical receiver that can comprise any of several conventional radiation detectors, such as a commercially available photosensor array or charge coupled device (CCD). The receiver is arranged such that it receives the radiation output from the radiation source which is reflected on the mask surface at a known angle and at known wavelengths.

In another implementation, an at-wavelength EUVL optical system is provided for EUVL patterning of a wafer. The optical system modulates radiation wavelength as a function of the angle of incidence on the reflective elements in the system, such as a mirror or reflective mask, to maximize the reflected radiation intensity and increase the system power efficiency (or throughput). Referring generally to FIG. 1A and FIG. 1B, the reflected radiation 185, 190, 195 comprising an image of the pattern associated with the patterned mask 115 is transmitted to an imaging system 145 and subsequently to an imaging target, such as a wafer 130.

A system designed to transmit a plurality of wavelengths, each wavelength corresponding to a specific angle of incidence on a reflective surface, provides an improvement in the resolution that can be achieved in imaging a pattern or a defect on a multi-layer coated reflective mask and an improvement in the power efficiency of an EUV optical system, including EUV lithography systems. By varying wavelength as a function of angle of incidence, the maximum numerical aperture, and hence the maximum resolution, of an optical system used in forming an image of a feature associated with a multi-layer coated reflective element is improved. In addition, the overall power throughput of EUV lithography systems may be increased and the EUV source power requirements may be decreased. Other implementations are within the scope of the following claims.

What is claimed is:

1. An apparatus comprising:
a source operative to generate radiation having a plurality of wavelengths;
a reflective mask including a multi-layer coating; and
means for simultaneously directing a plurality of said wavelengths to a position on the mask at different angles of incidence.

2. The apparatus of claim 1, wherein the radiation comprises wavelengths in a range of about 4 nm to 30 nm.

3. The apparatus of claim 1, wherein said means comprises:

a dispersive element operative to direct a plurality of said wavelengths to a different location on a first reflective element; and
a second reflective element operative to receive said plurality of said wavelengths and direct said wavelengths to the position on the mask at different angles of incidence.

4. The apparatus of claim 3, wherein the dispersive element includes a grating.

5. The apparatus of claim 4, wherein the grating comprises a holographic grating.

6. The apparatus of claim 4, wherein the grating comprises a ruled grating.

7. The apparatus of claim 6, wherein the ruled grating comprises between 10 and 50000 grooves per millimeter.

8. The apparatus of claim 1, wherein the radiation source is operative to emit said wavelengths at different angles, and further comprising:
a reflective element operative to receive said wavelengths and direct said wavelengths to the position on the mask at different angles of incidence.

9. The apparatus of claim 1, further comprising;
an imaging target; and
means for directing the plurality of said wavelengths from the mask to the imaging target at different angles of incidence.

10. The apparatus of claim 1, wherein the plurality of wavelengths comprise off-axis and on-axis wavelengths.

11. The apparatus of claim 10, wherein the off-axis wavelengths are shorter than the on-axis wavelengths.

12. The apparatus of claim 1, wherein the multi-layer coating comprises alternating layers of Si and Mo.

13. The apparatus of claim 1, wherein the multi-layer coating comprises alternating layers of Mo and Be.

14. The apparatus of claim 1, wherein the multi-layer coating comprises alternating layers of Mo, $B_4C$ and Si.

15. The apparatus of claim 1, wherein the wavelength corresponding to an angle of incidence on the mask is determined by the formula $\lambda = 2d\ n_{avg} \cos \theta$, wherein $n_{avg}$ is the real part of the average index of refraction at the wavelength $\lambda$ of the materials comprising the multi-layer, d is the period of the reflective coating, and $\theta$ is the incident angle of wavelength $\lambda$.

16. The apparatus of claim 1, wherein the wavelength corresponding to an angle of incidence on the mask is empirically determined by identifying increased reflectivity of a multi-layer coated reflective mask at a plurality of radiation wavelengths as a function of the angle of incidence.

17. An apparatus comprising:
a source operative to generate radiation having a plurality of wavelengths;
a dispersive element operative to direct a plurality of said wavelengths to a different location on a first reflective element;
a second reflective element operative to receive said plurality of said wavelengths and direct said wavelengths to the position on the mask at different angles of incidence, wherein each wavelength incident on the mask corresponds to a specific angle of incidence on said mask.

18. The apparatus of claim 17, further including an optically dispersive element.

19. The apparatus of claim 18, wherein the optically dispersive element includes a grating.

20. The apparatus of claim 17, wherein the apparatus further comprises an imaging target.

21. The apparatus of claim 20, wherein the imaging target is a wafer.

22. The apparatus of claim 20, wherein the imaging target is a detector.

23. The apparatus of claim 22, wherein the detector is a charge coupled device (CCD).

24. A method comprising:
inputting in to a system EUV radiation comprising a plurality of off-axis and on-axis wavelengths; and
determining the wavelength of each of the plurality of off-axis wavelengths as a function of the angle of incidence of the off-axis wavelength on at least one reflective surface comprised of a graded multi-layer coating.

25. The method of claim 24, wherein the radiation is produced by a source generating an angular emission spectrum of EUV radiation that varies with the emission wavelength.

26. The method of claim 24, wherein the radiation is produced by a source comprising an optically dispersive element.

27. The method of claim 26, wherein the optically dispersive element is a grating.

28. The method of claim 24, wherein the off-axis wavelengths are shorter than the on-axis wavelengths.

29. The method of claim 24, wherein the plurality of wavelengths comprise wavelengths from about 4 to 30 nm.

30. The method of claim 24, wherein the wavelength corresponding to an angle of incidence on the reflective element is determined by the formula $\lambda = 2d\, n_{avg} \cos \theta$, wherein $n_{avg}$ is the real part of the average index of refraction at the wavelength $\lambda$ of the materials comprising the multi-layer, d is the period of the reflective coating, and $\theta$ is the incident angle of wavelength $\lambda$.

31. The method of claim 24, wherein the wavelength corresponding to an angle of incidence on the reflective element is empirically determined by identifying increased reflectivity of a multi-layer coated reflective element at a plurality of radiation wavelengths as a function of the angle of incidence.

* * * * *